United States Patent [19]

Gibbs

[11] 3,990,451
[45] Nov. 9, 1976

[54] SURGICAL INSTRUMENT

[76] Inventor: Stephen D. Gibbs, 414-2nd St. SW., Watertown, S. Dak. 57201

[22] Filed: May 15, 1975

[21] Appl. No.: 577,796

[52] U.S. Cl. .............................. 128/305; 128/2 B; 30/358
[51] Int. Cl.² ........................................ A61B 17/32
[58] Field of Search .............. 128/305, 2, 355, 310, 128/329, 304, 303; 30/358, 130, 301, 316, 124, 306

[56] References Cited
UNITED STATES PATENTS

| | | | |
|---|---|---|---|
| 1,513,478 | 10/1924 | Bourque | 30/358 X |
| 3,502,070 | 3/1970 | Bliss | 128/2 B |
| 3,512,519 | 5/1970 | Hall | 128/2 |
| 3,561,449 | 2/1971 | Bellantoni | 128/305 |

FOREIGN PATENTS OR APPLICATIONS

| | | | |
|---|---|---|---|
| 136,813 | 8/1952 | Sweden | 30/306 |

Primary Examiner—John D. Yasko
Attorney, Agent, or Firm—Stuart J. Friedman

[57] ABSTRACT

A surgical instrument for making a closed periphery incision, preferably navicular in shape, comprises a handle including an enlarged cutting head rigidly mounted at one end thereof to prevent relative rotation between the handle and the cutting head, the head being hollow and defining a pair of elongated cutting blades arranged in generally side-by-side relation and including cutting edges therealong facing in generally the same direction, corresponding pairs of ends of the blades being convergent toward and joined with each other, and the cutting edges being outwardly convex in the direction in which they face. By virtue of at least one pair of corresponding blade edges intersecting to form an acute angle included therebetween, the incision is advantageously started by applying the corner defined by the intersecting blade edges to the skin with a firm pressure and then rocking the tool along its outwardly convex edges to complete the incision.

18 Claims, 6 Drawing Figures

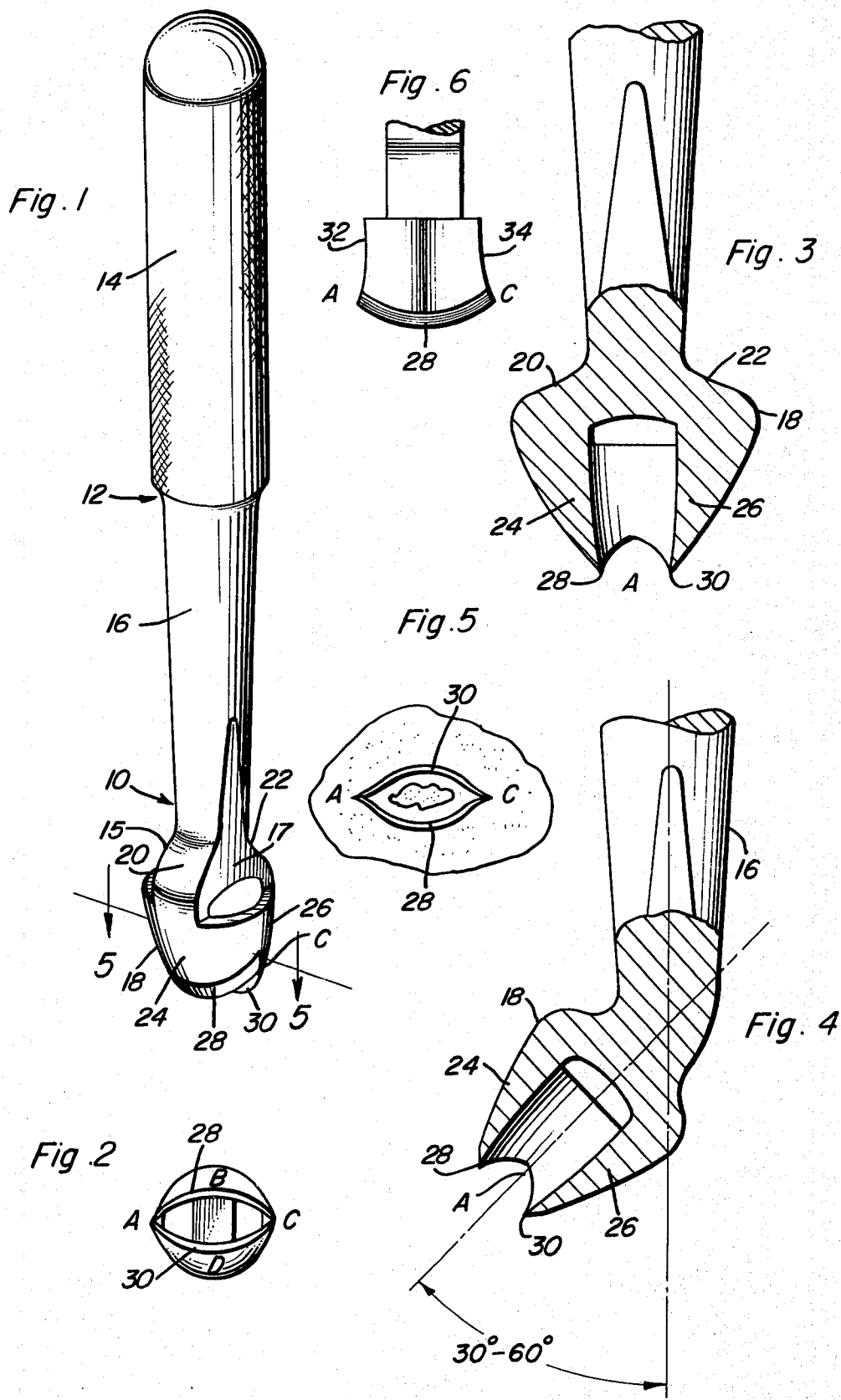

SURGICAL INSTRUMENT

The present invention relates to surgical instruments and, more particularly, to surgical instruments useful for excising lesions.

It is well known and generally accepted surgical practice to excise lesions by making a navicular-shaped incision around the lesion with a scalpel. To accomplish this, it is necessary to make two separate curved incisions representing the sides of the navicular shape by cutting with the scalpel blade and handle either perpendicular to the skin or tipped slightly away from the perpendicular in such a manner that the tip of the blade is directed away from the lesion. Care must be exercised to avoid crossing the incision lines at either end where they intersect. Following the incision, the lesion is removed by lifting at one of its corners using a tweezer or like device and by cutting with a scalpel across the base of the lesion to complete the excision. Again, care must be exercised to avoid nicking the edges of the sides of the incision.

Unfortunately, this simple surgical technique has many shortcomings. For example, it is not uncommon for the incision lines to cross or for the incision sides to be nicked during the procedure with the result that healing is slowed and the final appearance of the healed wound is adversely affected. Moreover, there is some difficulty when making curved incisions in maintaining the blade perpendicular to the skin and there is a tendency for the blade to be disposed at an angle to the skin such that the blade tip is directed toward the lesion. In such a case, subsequent suturing of the wound is made difficult because the skin has to be unnaturally stretched to bring the wound edges together. Finally, it is generally accepted that if the scar remaining after the wound heals is to be a fine, straight line scar, then the original incision must be a proper navicular shape. This shape is difficult to achieve when the scalpel is employed in a free-hand manner.

One partial solution to the problem of making a proper navicular incision is offered in U.S. Pat. No. 3,502,070 which recognizes the difficulty of making a properly shaped incision in a free-hand manner. It therefore proposes that the surgeon utilize a skin marker to impress a proper boat or navicular shape in the skin around the lesion, after which the surgeon makes his incision and removes the lesion in the conventional fashion. While the use of a marker is certainly a step toward improving the shape of the incision, it does not purport to solve the other problems encountered in the making of a navicular incision, i.e., the problems of crossed incision lines, nicked incision edges and incisions angled improperly relative to the lesion. In other words, the technique suggested in U.S. Pat. No. 3,502,070 still places virtually complete reliance on the skill of the surgeon with a scalpel.

It is therefore an object of the present invention to provide a surgical device for making a navicular-shaped incision.

It is another object of the invention to provide a surgical instrument which vertically cuts a properly shaped navicular incision around a lesion by the application of a firm pressure and rocking motion to the instrument.

It is still another object of the invention to provide a surgical instrument useful for excising lesions from the body cavities.

Other objects and advantages will become apparent from the following description and appended claims considered together with the accompanying drawings.

FIG. 1 is a perspective view of the surgical instrument of the present invention.

FIG. 2 is a bottom view of the instrument of FIG. 1.

FIG. 3 is a partial sectional view of another embodiment of the instrument of FIG. 1.

FIG. 4 is a partial sectional view of still another embodiment of the instrument of FIG. 1.

FIG. 5 is a sectional view taken substantially along line 5—5 in FIG. 1 showing the instrument applied to the skin of a patient emcompassing the lesion within its navicular-shaped cutting edges.

FIG. 6 is a partial elevational view of the cutting head of the instrument of FIG. 1 viewed along a plane perpendicular to the major axis of the navicular opening defined by the cutting edges.

Referring to the drawings and particularly to FIG. 1, there is shown generally at 10 the surgical instrument of the present invention. Instrument 10 is intended for making properly shaped incisions for the removal of various type growths or malformations, herein referred to generally as lesions. Instrument 10 consists of an elongated handle 12 having an upper, generally cylindrical knurled portion 14 and a lower shank portion 16 tapering to an enlarged, generally hollow cutting head 18.

Cutting head 18 is diametrically enlarged in a plane transverse to the longitudinal extent of the handle to define, with shank portion 16, at least one pair of diametrically opposite shoulders 20, 22 to which cutting pressure can be conveniently applied, as will be discussed more fully hereinafter. If desired, the cutting head can be enlarged around its entire periphery to form, in lieu of shoulders 20, 22, a circumferentially extending flange-type upper surface. Where the cutting head is enlarged around its entire periphery, cut-out portions 15 and 17, as shown in FIG. 1, would not be present. Depending from shoulders 20, 22 are cutting blades 24, 26, respectively. Each of the blades comprises a generally arcuate, outwardly bowed surface which, when viewed in a plane perpendicular to the plane of the shoulders (see FIG. 3), tapers inwardly and downwardly from the shoulders toward the free ends of the blades. The blades are disposed in facing relationship with their bowed surfaces opening toward each other and are joined at their corresponding ends to form a continuous cutting head. The cutting edges 28, 30 at the free ends of the blades define a generally navicular-shaped opening therebetween. A particularly important feature of the blades is that their cutting edges are outwardly convex in the direction away from handle 12 to form a rocker shaped cutting surface which facilitates making the navicular-shaped incision. Another important feature, shown most clearly in FIG. 2, is that the intersection of the bowed surfaces of the cutting edges define rather sharp corners A and C, i.e., the included angle between the edges is acute, rather than mere bends or curves, which facilitates starting the incision. If desired, the corners A and C can be made still sharper if the blade end intersections 32 and 34 are slightly inwardly concave, as can be most clearly seen when viewing the blades along a plane parallel to the shoulders (see FIG. 6). In this manner, corner A is defined by the intersection of concave end 32 and cutting edges 28 and 30 while corner C is defined by the intersection of concave end 34 and cutting edges 28 and 30.

The opening defined by the cutting edges, which is boat-shaped or football-shaped (referred to herein as "navicular") is most clearly seen in FIG. 2. Cutting edge 28 bows outwardly along a continuous arc from corner A (at one intersection of edges 28 and 30) through arc midpoint B to corner C (at the other intersection of edges 28 and 30). In similar manner, cutting edge 30 bows outwardly along a continuous arc from corner C through arc midpoint D to corner A. AC represents the major axis (or length) and BD represents the minor axis (or width) of the navicular opening. The length to width ratio of the opening is preferably 3, although it may advantageously vary between 2 and 4, depending upon the location of the lesion and the nature of the tissue at that particular location.

The surgical instrument of the present invention is desirably formed of stainless steel with at least the cutting edges formed of surgical grade steel which can readily be beveled. In order that a proper instrument is available for the removal of various sized lesions, the instrument, and particularly the cutting head, may be made in a number of sizes. One exemplary sized instrument has an over-all length from cutting edges to handle top of about 3¾ inches, a blade length from the shoulders to the cutting edges of about ½ inch, a shoulder width from handle periphery to outer shoulder edge of about ⅛ inch, and a navicular opening which is 7/16 inch in length and 3/16 inch in width. In use, the instrument may be grasped by the surgeon at the knurled handle or, more conveniently, held with the knurled handle in the palm of the hand and with the thumb and forefinger gripping the lower portion of the shank and resting on the shoulders. The instrument selected is properly sized for the particular lesion to be excised when, as shown in FIG. 5, the lesion is completely encompassed within the navicular shape of the cutting edges and healthy skin is visible between the lesion and the cutting edges completely around the lesion. To excise the lesion, the instrument is held at an acute angle to the skin and one corner of the cutting head, A or C, is pressed upon the skin at an appropriate point at one end of the lesion. A firm pressure applied to the instrument causes the corner to penetrate the skin to start the incision. By maintaining the pressure and rocking the instrument along its cutting edges toward the other corner, the navicular-shaped incision is completed to a depth, depending upon the instrument and the applied pressure, of from 3 to 5 millimeters, or about to the fat layer. To remove the navicular section including the lesion, the section should be lifted with a tweezer or like instrument and cut along its base with a scissors. Finally the remaining wound may be closed by suturing in the conventional manner.

It will be appreciated that using the instrument of the present invention to make a navicular-shaped incision around a lesion avoids the shortcomings of present surgical procedures in that (1) it insures that the incision is made perpendicular to the skin; (2) it avoids the possibility of crossed incision lines; (3) it insures a properly shaped navicular incision; and (4) it avoids the likelihood of nicking the sides of the incision. It will also be appreciated that the instrument can be modified to suit personal preferences and for particular uses without losing any of its inherent advantages. For example, the width of the shoulders can be increased to about ⅜ inch on each side of the handle, or as desired (see FIG. 3), to provide a larger area for applying finger pressure when making the incision. In another embodiment of the invention, particularly useful for making incisions within the body cavities, e.g., mouth, rectum, nose, vagina, ear, the cutting head is disposed at an angle of from 30° to 60°, preferably 45°, to the handle (see FIG. 4). The angle is preferably formed in the plane of the shoulders or in a plane parallel to the plane of the minor axis of the navicular opening. Moreover, it will also be appreciated that the advantages of this invention are not necessarily limited to forming navicular-shaped incisions. If it is desirable to form incisions having other shapes, particularly shapes which include at least one corner therein defining an included acute angle, in order that the incision can be readily started and thereafter completed using the simple rocking technique of the present invention, the opening defined by the cutting edges can be modified as necessary.

While the present invention has been described with reference to particular embodiments thereof, it will be understood by those skilled in the art that numerous modifications can be made without actually departing from the scope of the invention. Accordingly, all modifications and equivalents may be resorted to which fall within the scope of the invention as claimed.

What is claimed as new is as follows:

1. A surgical instrument for making a closed periphery incision in the skin, said instrument including handle means and a pair of elongated cutting blade portions extending therefrom and rigidly mounted on said handle means to prevent relative rotation between said handle means and said blade portions, said blade portions arranged in generally facing relation and terminating in cutting edges extending therealong, said edges defining a closed periphery opening therebetween, the cutting edges of at least one pair of corresponding blade portion ends being coextensive and intersecting at an acute angle included between said cutting blade portions, said edges facing outwarding of said opening in a direction generally away from said handle means and being outwardly convex in the direction in which said edges face to define rocker-shaped cutting edges, whereby said incision is started by penetrating said skin with said included acute angle intersection of said edges and conveniently completed in a single rocking motion of said rocker-shaped cutting edges over the skin.

2. An instrument, as claimed in claim 1, wherein said closed periphery opening is navicular in shape.

3. An instrument, as claimed in claim 2, wherein the length of said navicular opening is two to four times greater than the width of said opening.

4. A surgical instrument for making a closed periphery navicular shaped incision in the skin comprising a handle including a cutting head rigidly mounted at one end thereof to prevent relative rotation between said handle and said head, said head being hollow and defining a pair of opposite side cutting blade portions, said blade portions having bowed cutting edges opening toward each other and being joined at their corresponding ends to define a navicular shaped opening therebetween, said cutting edges facing outwardly of the end of said opening remote from said handle and being outwardly convex in the direction in which they face to thereby define rocker-shaped cutting edges whereby said navicular incision is conveniently made in a single rocking motion of said rocker-shaped cutting edges over the skin.

5. An instrument, as claimed in claim 4, wherein said cutting head is enlarged to define with said handle at least one pair of shoulders facing toward said handle.

6. An instrument, as claimed in claim 4, wherein the length of said navicular opening is two to four times greater than the width of said opening.

7. An instrument, as claimed in claim 6, wherein the length of said navicular opening is about three times greater than the width of said opening.

8. An instrument, as claimed in claim 5, wherein each of said shoulders extends outwardly from said handle a distance of at least about ⅜ inch.

9. An instrument, as claimed in claim 4, wherein said head forms with said handle an excluded angle of from 30° to 60°.

10. An instrument, as claimed in claim 9, wherein said head forms an excluded angle of about 45° with said handle.

11. An instrument, as claimed in claim 9, wherein said angle lies in a plane substantially parallel to the plane in which the minor axis of said navicular opening lies.

12. An instrument, as claimed in claim 5, wherein said shoulders are spaced apart by said handle.

13. An instrument, as claimed in claim 4, wherein said cutting edges intersect to form sharp included angles therebetween for ease in starting the navicular shaped incision.

14. An instrument, as claimed in claim 13, wherein said opposite side cutting blade portions are elongated and joined along their length to define at least one elongated blade portion joint, said joint is inwardly concave along its length to define, with the corresponding intersection of said cutting edges, a sharp pointed corner for ease in starting the navicular shaped incision.

15. An instrument, as claimed in claim 14, wherein said blade portions define a pair of joints, said joints and the corresponding intersections of said cutting edges defining a pair of sharp pointed corners.

16. An instrument, as claimed in claim 14, wherein said cutting head is integral with said handle and enlarged to define therewith at least one pair of shoulders facing said handle.

17. A surgical instrument comprising an elongated handle and a hollow cutting head rigidly mounted at one end of said handle to prevent relative rotation between said handle and said head, said head being enlarged relative to said handle in a first transverse diametric plane to define with said handle at least one pair of diametrically opposite shoulders facing toward the other end of said handle, said head including a pair of elongated cutting blades depending from said shoulders and arranged in generally facing relation, each of said blades terminating at its free end in a cutting edge, said cutting edges facing in the same direction and defining a closed periphery navicular shaped opening therebetween, said opening having a major axis to minor axis ratio of from 2:1 to 4:1, said blades being convergent toward and joined with each other at their corresponding ends and bowed away from each other intermediate their corresponding ends, said cutting edges facing oppositely of said other end of said handle and being outwardly convex in the direction in which they face.

18. An instrument, as claimed in claim 17, wherein said major axis extends in a second transverse diametric plane, said first and second planes disposed substantially normal to each other.

* * * * *